US010184900B2

(12) United States Patent
Leconte et al.

(10) Patent No.: US 10,184,900 B2
(45) Date of Patent: Jan. 22, 2019

(54) METHOD, DEVICE AND INSPECTION LINE FOR VISUALIZING THE FLATNESS OF A SURFACE OF A CONTAINER RING

(71) Applicant: TIAMA, Vourles (FR)

(72) Inventors: Marc Leconte, Loire sur Rhone (FR); Michel Ollivier, Acigne (FR)

(73) Assignee: TIAMA, Vourles (FR)

( * ) Notice: Subject to any disclaimer, the term of this patent is extended or adjusted under 35 U.S.C. 154(b) by 85 days.

(21) Appl. No.: 15/518,535

(22) PCT Filed: Oct. 14, 2015

(86) PCT No.: PCT/FR2015/052762
§ 371 (c)(1),
(2) Date: Apr. 12, 2017

(87) PCT Pub. No.: WO2016/059343
PCT Pub. Date: Apr. 21, 2016

(65) Prior Publication Data
US 2017/0241916 A1 Aug. 24, 2017

(30) Foreign Application Priority Data
Oct. 17, 2014 (FR) ...................... 14 59977

(51) Int. Cl.
*G01N 21/90* (2006.01)
*G06T 7/62* (2017.01)
(Continued)

(52) U.S. Cl.
CPC ....... *G01N 21/9054* (2013.01); *G01B 11/306* (2013.01); *G06T 7/0004* (2013.01);
(Continued)

(58) Field of Classification Search
CPC ......... G01N 21/9054; G01N 2201/061; G01N 2021/845; H04N 5/2256; H04N 5/2252; G06T 7/62; G06T 7/0004; G01B 11/306
(Continued)

(56) References Cited

U.S. PATENT DOCUMENTS

| 3,390,569 A | 7/1968 | McMeekin |
| 4,606,435 A | 8/1986 | Miyazawa et al. |

(Continued)

FOREIGN PATENT DOCUMENTS

| DE | 29 16 361 | 11/1980 |
| DE | 20 2012 104043 | 11/2012 |

(Continued)

OTHER PUBLICATIONS

Symplex Hexkon, Seal Face-/Closure Wall Inspection, Industrielle Inspektionstechnik, 2005.

*Primary Examiner* — Tung T Vo
*Assistant Examiner* — Joseph W Becker
(74) *Attorney, Agent, or Firm* — Clark & Brody

(57) ABSTRACT

A method of visualizing the planeness of a ring surface of a container includes lighting the ring surface from above using a peripheral incident light beam having radial rays with specular reflection on the ring surface. An optical system is used to form a plane image of the ring surface on a sensor, with an optical geometrical transformation that converts a real height difference (dZ) into an image radial offset (dR) on the image, and the image radial offset (dR) corresponding to a unit real height difference (dZ) is greater than the image radial offset corresponding to a real radial offset of the same dimension. A device and an installation implementing the visualizing method is also disclosed.

27 Claims, 7 Drawing Sheets

(51) Int. Cl.
  *G01B 11/30* (2006.01)
  *G06T 7/00* (2017.01)
  *H04N 5/225* (2006.01)
  *G01N 21/84* (2006.01)

(52) U.S. Cl.
  CPC ............ *G06T 7/62* (2017.01); *H04N 5/2252* (2013.01); *H04N 5/2256* (2013.01); *G01N 2021/845* (2013.01); *G01N 2201/061* (2013.01)

(58) Field of Classification Search
  USPC ..................................................... 348/86–92
  See application file for complete search history.

(56) References Cited

U.S. PATENT DOCUMENTS

| | | |
|---|---|---|
| 4,758,084 A | 7/1988 | Tokumi et al. |
| 4,914,289 A | 4/1990 | Nguyen et al. |
| 4,959,538 A | 9/1990 | Swart |
| 5,072,107 A | 12/1991 | Apter |
| 5,661,294 A | 8/1997 | Buchmann et al. |
| 5,699,152 A | 12/1997 | Fedor et al. |
| 6,049,389 A | 4/2000 | Volay et al. |
| 6,072,575 A | 6/2000 | Loll |
| 6,172,748 B1 | 1/2001 | Sones et al. |
| 6,654,116 B1 | 11/2003 | Kwirandt |
| 6,903,814 B1 | 6/2005 | Juvinall et al. |
| 2001/0048524 A1 | 12/2001 | Sones |
| 2004/0150815 A1 | 8/2004 | Sones et al. |
| 2004/0263620 A1 | 12/2004 | Diehr |
| 2006/0051086 A1 | 3/2006 | Schroter et al. |
| 2006/0126060 A1 | 6/2006 | Colle et al. |
| 2006/0176474 A1 | 8/2006 | Lehn et al. |
| 2008/0186693 A1 | 8/2008 | White et al. |
| 2009/0066944 A1 | 3/2009 | Gauffre et al. |
| 2016/0059343 A1 | 3/2016 | Nam et al. |

FOREIGN PATENT DOCUMENTS

| | | |
|---|---|---|
| EP | 0047936 | 3/1982 |
| EP | 0 657 732 | 6/1995 |
| FR | 2846422 | 4/2004 |
| FR | 2884611 | 10/2006 |
| FR | 2896041 | 7/2007 |
| JP | 2009-150767 | 7/2009 |
| WO | 2008/129650 | 10/2008 |

METHOD, DEVICE AND INSPECTION LINE FOR VISUALIZING THE FLATNESS OF A SURFACE OF A CONTAINER RING

The invention relates to the field of inspecting containers, in particular glass containers, and more precisely to verifying the planeness of the ring surface of such containers.

The ring surface is the top surface or top edge of the ring of the container. The ring surface is of annular shape about a theoretical central axis of the ring and it is thick to a greater or lesser extent along a direction that is radial relative to the theoretical axis. In theory, this surface is plane in a plane that is perpendicular to the theoretical central axis, in the sense that it presents at least one line of contact that is continuous over 360° around the axis with this plane, and it is perfectly circular. While being plane in the above sense, its profile in sections on a radial plane containing the theoretical central axis may have various shapes: the profile may be flat, rounded, upside-down V-shape, etc.

In numerous applications, the ring surface is the surface that comes into contact with the gasket of the lid or the cap. When the ring surface is not plane, there might be leaks after closure. It is thus important to be aware of planeness defects in the ring surface. These planeness defects may be analyzed at a given point on the surface of the ring as being a difference in height, which should be understood in this text as being a difference in position along a direction parallel to the theoretical central axis of the ring of the container, between a given point of the real ring surface of the container and a corresponding point of a theoretical ring surface. These two points correspond in that, in a system of cylindrical coordinates centered on the theoretical central axis, the corresponding points have the same angular coordinate, and one of them lies on the real ring surface while the other one lies on the theoretical ring surface. The theoretical ring surface is thus plane relative to a reference plane perpendicular to the theoretical central axis. This reference plane may be associated with the container in question, and for example it may correspond to the height of the highest point of the real ring surface, to the height of the lowest point of the real ring surface, to a mean height of the ring surface over its angular extent, etc. . . . . The reference plane may also be defined independently of the container, e.g. with reference to a display, inspection, or measurement device.

Planeness defects of the ring surface are often subdivided into at least two types, defects of the "glass missing" type are associated with problems of filling the mold for the ring with molten glass during fabrication. They are characterized by differences in height that extend over a small angular amplitude around the theoretical axis. Defects of the "warped ring" type are height errors that are generally smaller, extending over a larger angular amplitude around the theoretical axis, but are nevertheless troublesome defects, often due to sagging, to problems with extracting articles from the mold, or to thermal problems.

At present, planeness defects are mainly detected by a "bell" system by detecting gas leaks. The residual leak is measured when a plane metal surface is pressed on the ring. The drawback of such inspection is that it does not provide information for evaluating the amplitude of the defect, but only gives a binary indication (leak/no leak) indicative of whether or not the surface is plane. Such a system requires mechanical means for relative movements between the container and the device, which means are not only expensive but also slow down the throughput of the inspection line: the bell is raised and lowered, the article stops temporarily under the bell, etc. . . . . Furthermore, there is a real advantage in eliminating any contact with the ring of the article in order to avoid risks of breakage or of pollution.

Viewing systems are also known in which rings are observed using at least two high-angle or low-angle views. Diffuse lighting situated opposite from the cameras relative to the articles is used to light the article for inspection in transmission. The drawback of that system is that it requires at least two cameras and two light sources, and possibly two telecentric optical systems with their supports and adjustments. The installation is expensive and requires long light paths, which means that it occupies a large amount of space.

To remedy those drawbacks, and as set out above, proposals have already been made to use cameras that are already there for performing another inspection of the container, e.g. inspecting the appearance of the shoulder if the container is a bottle made of glass. Nevertheless, that makes it necessary to select positions for the inspection device that can only be a compromise between settings for detecting defects in the shoulder zone and settings for detecting geometrical defects of the ring surface. Such compromises are unsatisfactory both for the originally intended measurement and for the attempt at measuring planeness with those cameras.

By increasing the number of viewing angles, in particular by combining similar views with different low angles and high angles, it is also possible to take three-dimensional (3D) measurements of portions of the ring and then to unite those measurements in order to reconstitute the overall shape of the ring surface by computation. That requires a plurality of optical images to be acquired. The optical images are then combined in pairs by algorithms for putting points into correspondence in pairs, on the basis of which real points with 3D coordinates are calculated by triangulation. The technique is that of stereo vision with complex algorithms. A plurality of stereo vision views are needed, thus requiring four or six cameras, for example. Those systems can be accurate, but they are very expensive and they occupy a large amount of space. Numerous parameters lead to that accuracy not being conserved over long-duration operation.

Document U.S. Pat. No. 6,172,748 describes a device having a plurality of distinct light sources that light the ring from below, i.e. from a point situated below a plane perpendicular to the axis of the ring and tangential to the surface of the ring. That device has a plurality of distinct mirrors, each providing an image of only an angular sector of the ring. Furthermore, even if the images overlap, azimuth angular discontinuity remains between the images because, at a potential overlap point in two images, there is a break of viewpoints for the overlap point in each of the images. That requires the image to be reconstituted by computer, which requires algorithms that are complex.

An object of the invention is thus to propose a display device for viewing planeness defects of a ring surface that is simpler than existing systems.

For this purpose, the invention provides a visualization method for visualizing the planeness of a real ring surface of a container, the ring surface having a theoretical shape that is plane and annular or circular around a theoretical central axis, and the method being of the type comprising the steps consisting in:

lighting the real ring surface of the container with a peripheral incident light beam; and using an optical system to form a plane image of the ring surface of the container on a two-dimensional photoelectric sensor;

the method being characterized in that:

the peripheral incident light beam comprises radial light rays contained in a radial plane containing the theoretical central axis, said radial rays being directed towards the theoretical central axis;

the peripheral incident light beam lights the ring surface from above, and radial rays of the incident light beam are reflected by specular reflection the ring surface;

in that the step consisting in forming a plane image includes an optical geometrical transformation that converts the real ring surface into a ring surface image, this transformation theoretically converting the theoretical ring surface into a theoretical ring surface image;

in that the optical geometrical transformation converts a real height difference along the direction of the theoretical central axis between a point under consideration of the real ring surface and a corresponding point of the theoretical ring surface into an image radial offset in the image of the image point of the ring surface image of the container relative to the corresponding image point of the theoretical ring surface image; and in that, in the plane image, the image radial offset corresponding to a unit real height difference is greater than the image radial offset corresponding to a real radial offset of the same dimension between said point under consideration of the real ring surface and a corresponding point of the theoretical ring surface.

According to optional other characteristics of such a method:

the image radial offset corresponding to a unit real height difference is at least three times greater than the image radial offset corresponding to a real radial offset of the same dimension between a point under consideration of the real ring surface and a point corresponding to the theoretical ring surface;

the method includes the step of observing the real ring surface by means of the optical system at an observation elevation angle of less than 25° relative to a plane perpendicular to the theoretical central axis;

the method includes the step of observing the real ring surface by means of the optical system at an observation elevation angle of less than 18.43° relative to a plane perpendicular to the theoretical central axis;

the optical system defines a peripheral observation field that observes the ring surface by radial observation rays that are contained in a radial plane containing the theoretical central axis and forming, relative to a plane perpendicular to the theoretical central axis, a theoretical central angle of less than 25°;

the observation elevation angle is less than 18.43° relative to a plane perpendicular to the theoretical central axis;

the optical system includes a primary reflection surface, the primary reflection surface being a surface of revolution having the theoretical central axis as its axis and arranged to reflect light rays coming from the real ring surface at the observation angle directly or indirectly towards the sensor;

the step consisting in forming a plane image includes optically forming a complete and continuous two-dimensional image of the real ring surface;

the peripheral incident light beam includes non-parallel radial rays in a common radial plane; and the incident beam lights the ring surface at an angle of incidence such that, at the point of reflection of an incident ray giving rise to a ray reflected by the real ring surface that is seen by the sensor, the normal to the ring surface forms an angle of less than 30° relative to the direction of the theoretical central axis.

The invention also provides a method of determining the planeness of a real ring surface of a container, the ring surface having a theoretical shape that is plane and annular about a theoretical central axis, the method being characterized in that it includes the visualization method having any preceding characteristics, and in that the method includes a determination step comprising determining an image radial offset between a line representative of the image of the ring surface and a theoretical line representative of the theoretical image of the ring surface.

In such a method, the line representative of the ring surface image may be the image formed by the optical system on the sensor of the reflection of the incident beam on the ring surface.

The invention also provides a display device for viewing the planeness of a real ring surface of a container, the ring surface having a theoretical shape that is plane and annular or circular around a theoretical central axis, the device being of the type in which it presents an installation zone for installing a container, said installation zone having an installation axis, of the type comprising:

a lighting system suitable for supplying a peripheral incident light beam having radial rays contained in a radial plane containing the installation axis, said radial rays being directed towards the installation axis;

a two-dimensional photoelectric sensor; and an optical system interposed between the container installation zone and the sensor and suitable for forming on the sensor an image of the ring surface of a container placed in the installation zone;

and of the type in which the lighting system, the sensor, and the optical system are arranged above the installation zone;

the device being characterized in that the optical system defines a peripheral observation field that observes the ring surface with radial observation rays that are contained in a radial plane containing the installation axis and that form an observation elevation angle of less than 25 degrees relative to a plane perpendicular to the installation axis; and in that the lighting system comprises a light source having the installation axis as its axis and presenting a diameter greater than the diameter of the ring surface.

According to optional other characteristics of such a device:

the device includes a single two-dimensional photoelectric sensor on which a complete and continuous image of the real ring surface is formed;

the device includes a primary reflection surface, the primary reflection surface being a surface of revolution having the installation axis as its axis and arranged to reflect light rays coming from the real ring surface at an observation elevation angle directly or indirectly towards the sensor;

the primary reflection surface reflects light rays indirectly towards the sensor, and the device includes at least one second reflection surface between the primary reflection surface and the sensor;

the primary reflection surface comprises a surface of revolution facing away from the installation axis and presenting a small diameter and a large diameter, both of which are smaller than the smallest diameter of the theoretical ring surface;

the primary reflection surface is a convex frustoconical surface presenting a half-angle at the apex equal to 45° minus half the observation elevation angle;

the primary reflection surface comprises a surface of revolution facing towards the installation axis and presenting a small diameter and a large diameter, both of which are greater than the greatest diameter of the theoretical ring surface so as to deflect light rays coming from the real ring surface at an observation elevation angle towards the installation axis, said rays being intercepted by a deflector reflection surface that comprises a surface of revolution facing away from the installation axis so as to deflect the rays towards the sensor;

the path followed by the rays between the primary reflection surface and the deflector reflection surface is perpendicular to the installation axis;

the deflector reflection surface comprises a convex frustoconical surface of revolution having the installation axis as its axis and presenting a half-angle at the apex of 45°;

the device includes a telecentric optical system between the sensor and the primary reflection surface;

the incident peripheral beam comprises non-parallel radial rays in a common radial plane;

the light source is an annular source forming a body of revolution having the installation axis as its axis; and the device has a housing containing the sensor, the objective system, a primary reflection surface, and optionally a deflector reflection surface.

The invention also provides an inspection line for inspecting containers each presenting a ring surface, the line being of the type in which the containers are moved on a conveyor line by a conveyor that transports the containers in a horizontal travel direction perpendicular to a theoretical central axis of each container, such that the containers thus present their ring surfaces in an upwardly-facing horizontal plane, the line being characterized in that the installation includes a device having any of the preceding characteristics, that is arranged on the installation with its installation axis in a vertical position, in such a manner that the observation field and the incident light beam are downwardly oriented towards the installation zone which is situated between the device and a transport member of the conveyor.

In such an inspection line, the conveyor may bring the containers in such a manner that their theoretical central axes coincide with the installation axis, and when they coincide, an image is acquired using the device without the device contacting the container.

Various other characteristics appear from the following description with reference to the accompanying drawings, which show embodiments of the invention as non-limiting examples.

FIGS. 1A and 1B are diagrammatic axial section views showing a device of the invention for performing a method of the invention, in which FIG. 1A shows observation rays illustrating the view of the photoelectric sensor, and FIG. 1B shows the paths of incident rays coming from the light source and reflected by the ring surface of a container towards the sensor through the optical system.

Figure 2A:
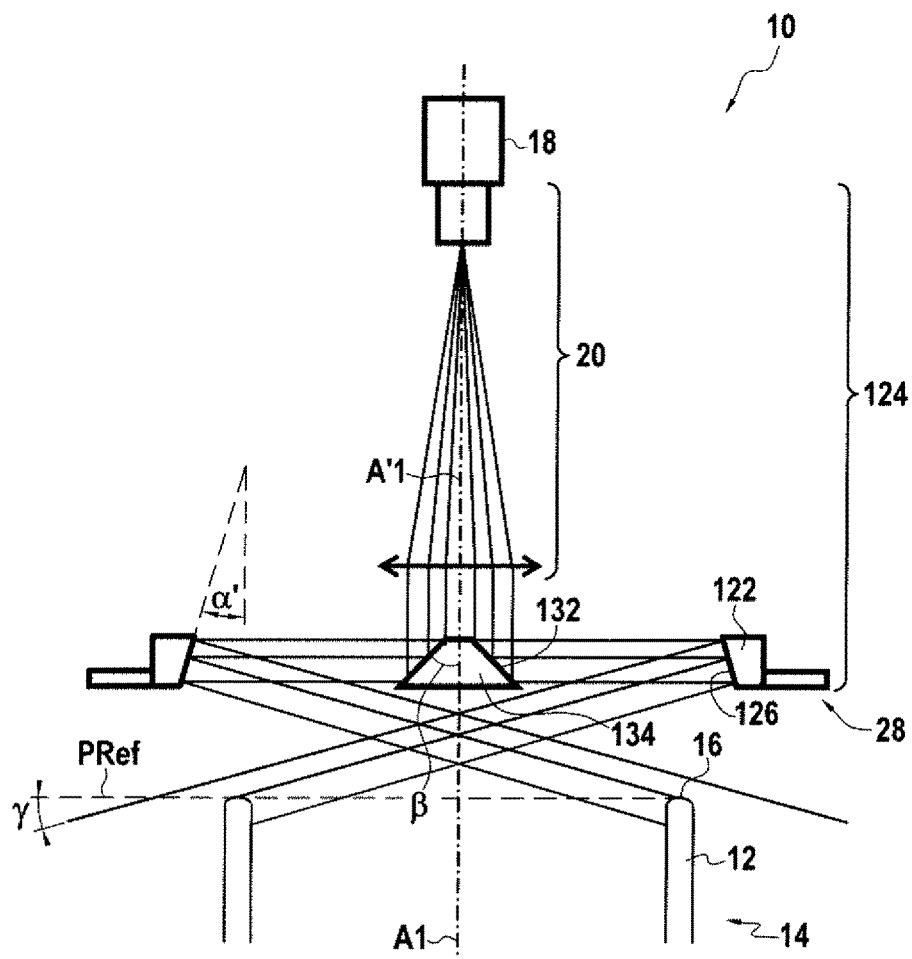
FIG. 2A is a view similar to FIG. 1A showing a second device of the invention for performing a second method of the invention.
Figure 3:
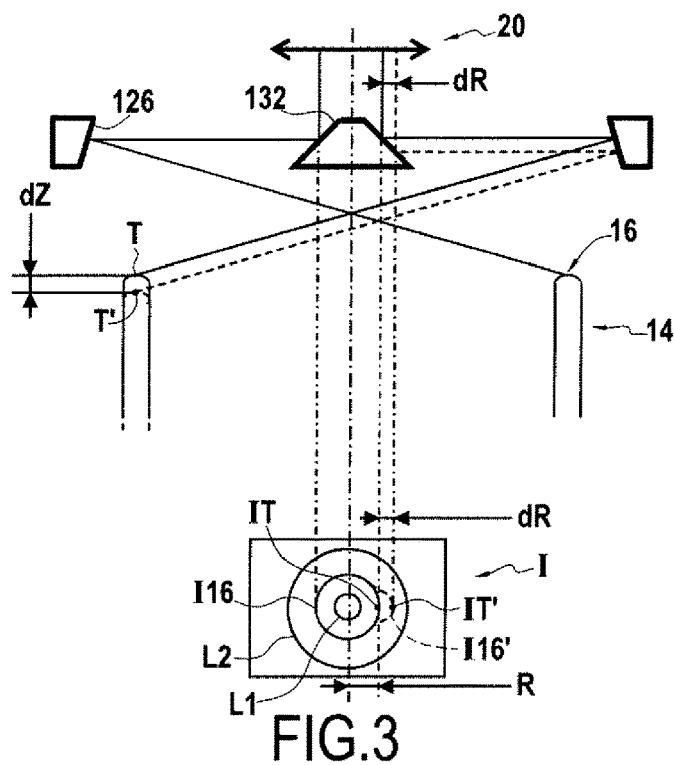

FIG. 3 is a diagram relating to the device and the method of FIG. 2A showing how the optical geometrical transformation converts a real height difference along the direction of the theoretical central axis between a point of the real ring surface and a corresponding point on the theoretical ring surface, into an image radial offset in the image of the point associated with the image of the ring surface of the container relative to the associated point of the theoretical image of the ring surface.

Figure 4:
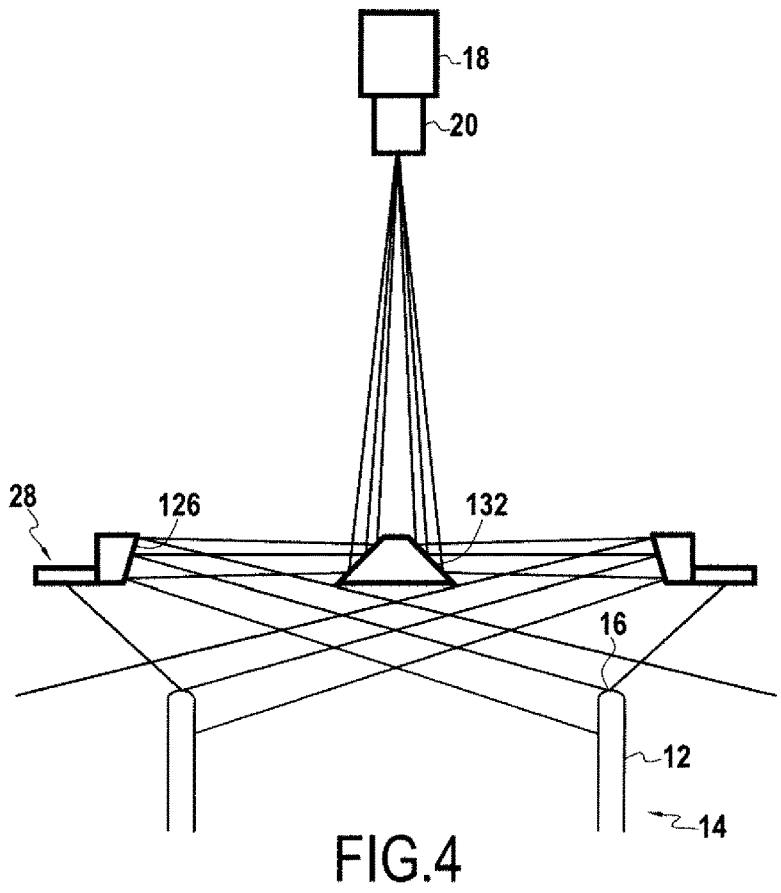

FIG. 4 is a diagram showing a variant of the FIG. 2A device and method, in which the optical system is not telecentric.

Figure 5A:
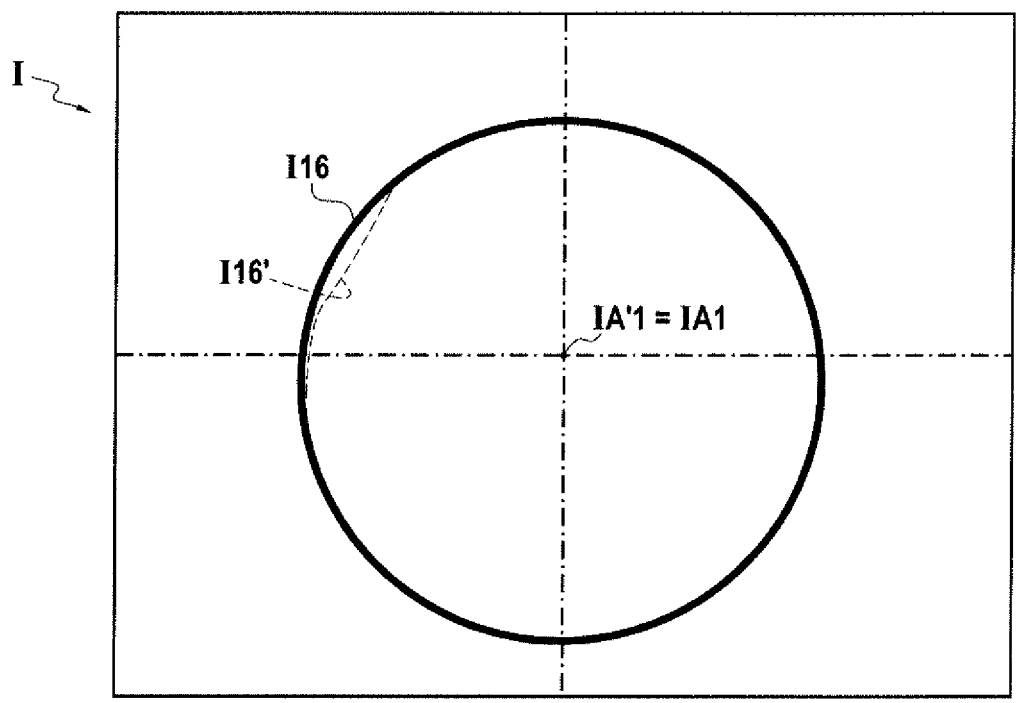
Figure 5B:
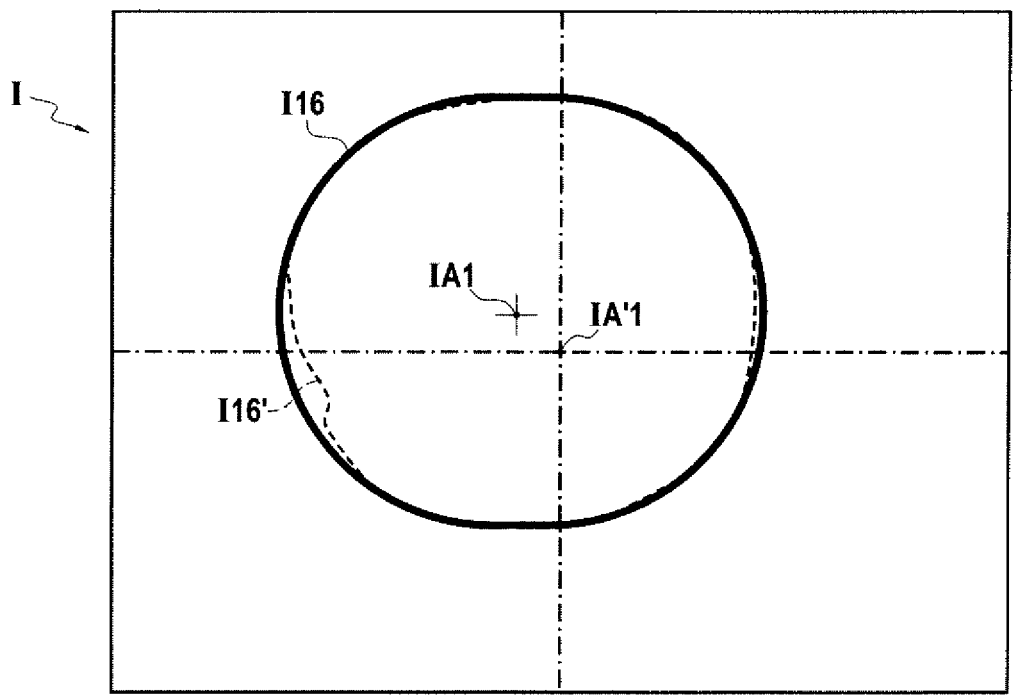

FIGS. 5A and 5B are diagrammatic views showing two examples of images acquired by a method and a device of the invention.

Figure 6:
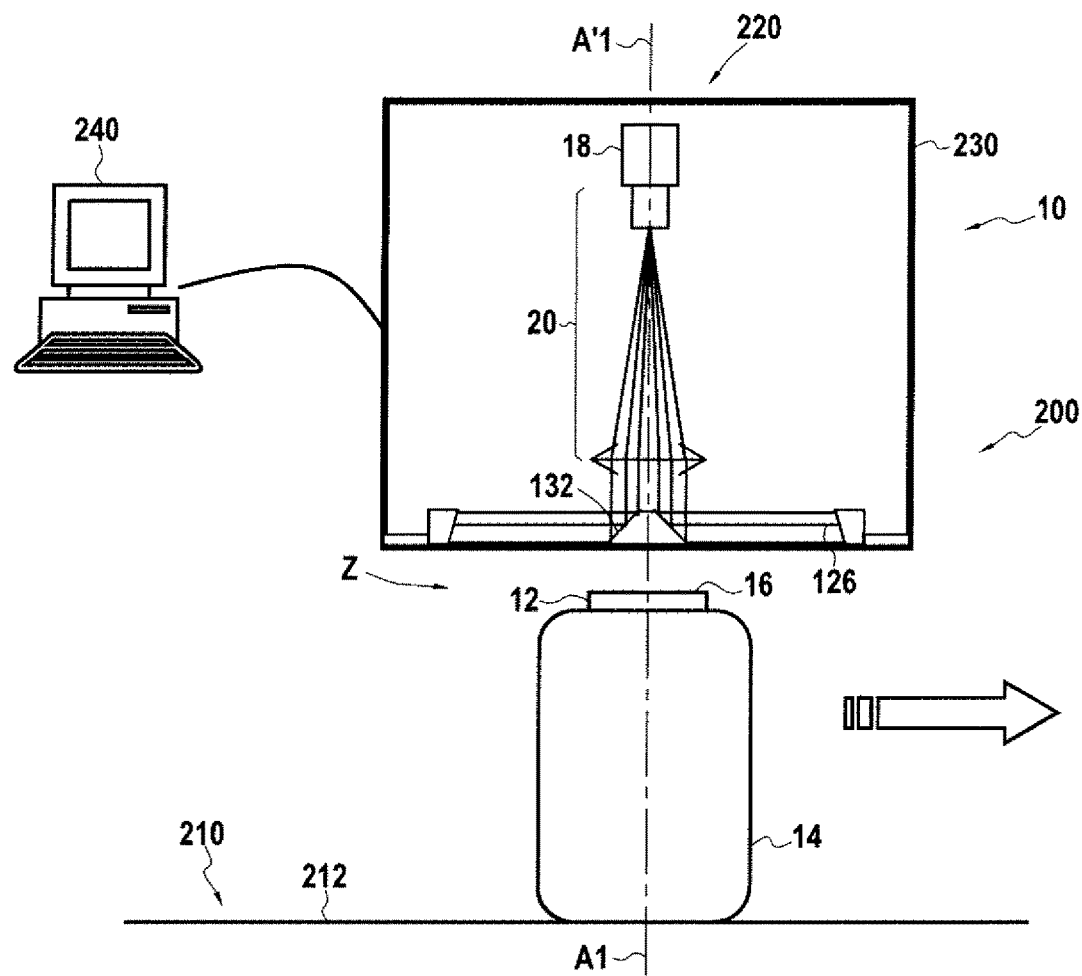

FIG. 6 is a diagrammatic view of an installation for inspecting containers and including a device of the invention.

Figure 1A:
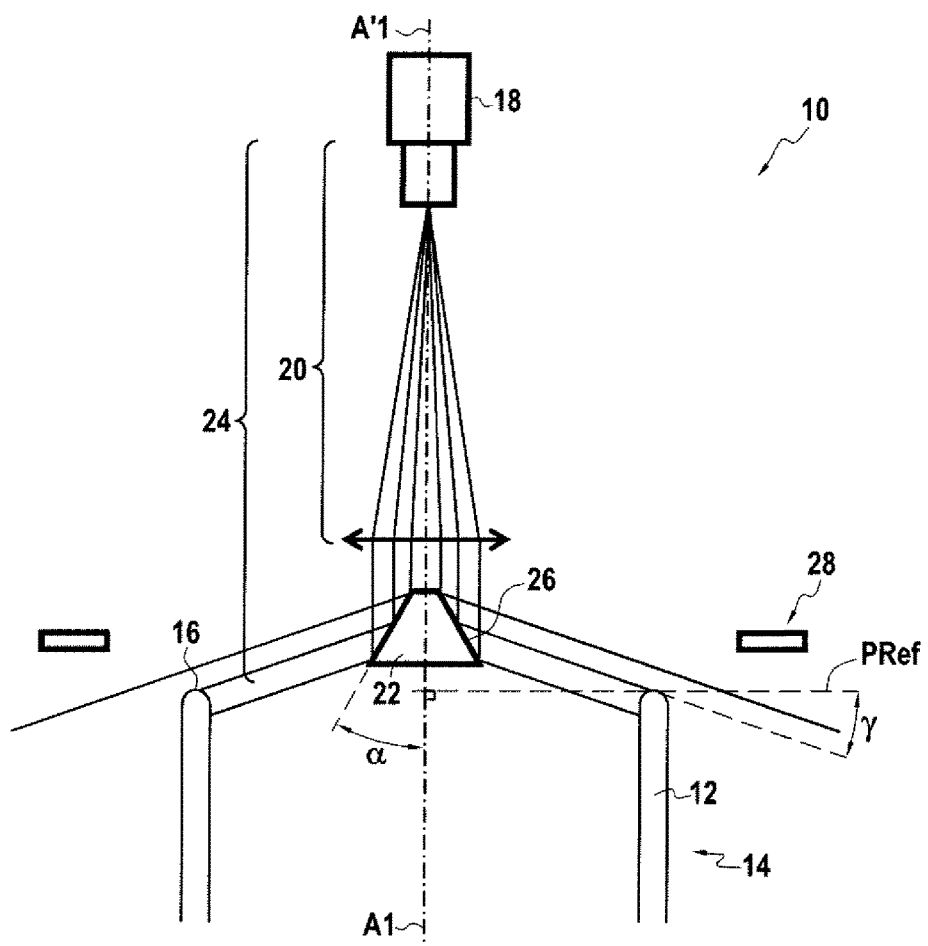
Figure 1B:
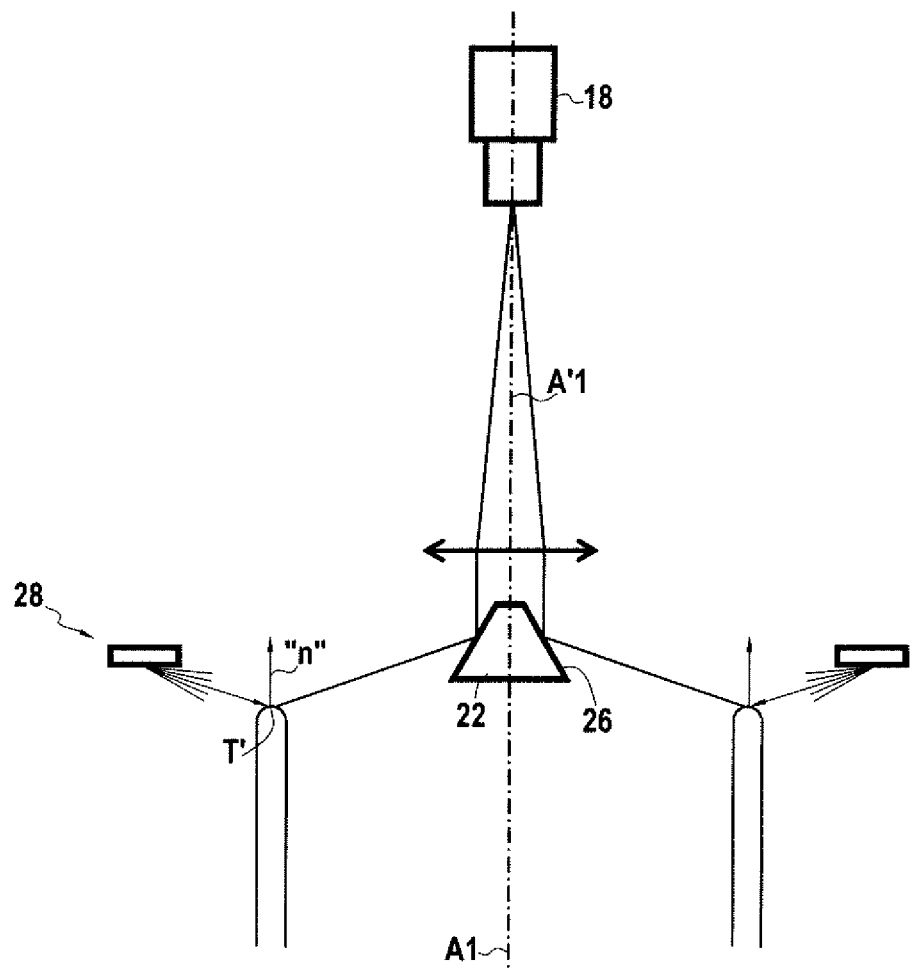
Figure 1C:
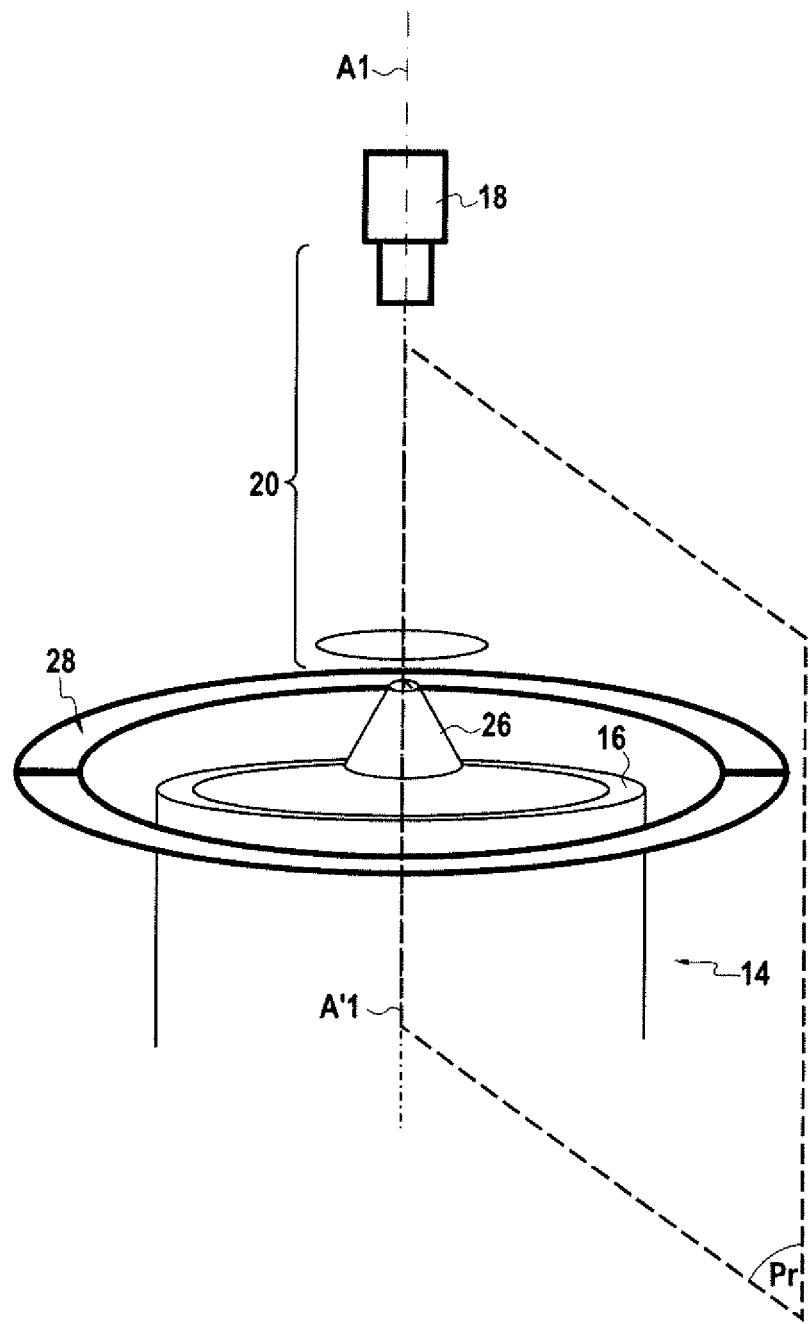
FIG. 1C is a diagrammatic perspective view of the embodiment of FIGS. 1A and 1B.

FIGS. 1A to 1C show a display device for viewing the planeness of a real ring surface of a container, the device performing a method of the invention. FIGS. 1A to 1C show only the top portion of the ring 12 of a container 14. A container 14 is defined as being a hollow container defining an inside volume that is closed over its entire periphery except at a top ring 12 that is open at one end.

For convenience, and solely by way of arbitrary definition, it is assumed that the container has a theoretical central axis A1 defined as being the theoretical central axis of its ring 12. It is also assumed arbitrarily that the ring is arranged at the top end of the container. Thus, in the present text, the concepts of high, low, top, and bottom are relative values corresponding to the orientation of the device 10 and of the container 14 as shown in the figures. Nevertheless, it should be understood that the invention can be implemented at any absolute orientation in three-dimensional space, insofar as the various components continue to be arranged with the same relative arrangement.

The ring 12 of the container is a circular cylinder about the axis A1. The body of the container (not shown) may also optionally be a body of revolution. The ring 12 is connected via its bottom end (not shown) to the remainder of the body of the container, while its free other end, referred to as the "top" end as an arbitrary assumption in the context of the present description, is terminated by a ring surface 16. Theoretically, the ring surface 16 is plane and parallel to a plane perpendicular to the axis A1, in the sense that it presents at least one line of contact with such a plane that is continuous over 360° around the theoretical central axis, and it is theoretically circular or annular in the plane. In the present text, a distinction is drawn between the real ring surface of the container and a theoretical ring surface. The theoretical ring surface is thus a plane surface in a reference plane perpendicular to the theoretical central axis A1. This reference plane may be defined as being associated with the container in question, such as the reference plane PRef in FIG. 1A, which is tangential to a point of the real ring surface 16, e.g. its highest point along the direction of the theoretical central axis A1. Alternatively, this reference plane may for example be situated at the lowest height of the real ring surface, or at a mean height of the ring surface over its angular extent, etc. The reference plane may also be defined independently of the container, e.g. with reference to one of the elements of the display device 10, e.g. with reference to a bottom surface of a housing of the device 10.

Viewing planeness thus consists essentially in viewing and possibly quantifying a position offset along the direction of the theoretical central axis A1 between a given point of the real ring surface and a corresponding point of the theoretical ring surface. These two points correspond in that in a system of cylindrical coordinate centered on the theoretical central axis, the corresponding points have the same angular coordinates, with one of them belonging to the real ring surface and the other to the theoretical ring surface. In other words, ignoring differences of radial position, they are arranged vertically one above the other along the axial direction of the theoretical central axis A1.

In order to enable the container to be inspected correctly, it is appropriate to take care that the container is properly presented in front of the display device 10. For this purpose, the device 10 of the invention has an installation zone in which the container is to be installed. This installation zone may be defined by an installation axis A'1 and by an installation plane (not shown) defined as being a plane perpendicular to the installation axis A'1 and situated level with the lowest point of the device. Thus, in order to be correctly inspected, a container needs to be presented in such a manner that its theoretical central axis A1 corresponds as closely as possible with the installation axis A'1, and that its ring is presented with its open top end facing towards the device 10 but below the installation plane. Ideally, the two axes A1 and A'1 coincide. It can be understood that the entire display device 10 of the invention can be positioned above the installation plane with the container being brought in below the installation plane without any risk of making contact with the device. The container 14 can thus be brought in using any movement in translation along a direction perpendicular to the installation axis A'1, without risk of interfering with the device 10.

The device and the method of the invention make use of a two-dimensional photoelectric sensor 18 for acquiring a two-dimensional image of the real ring surface of the container. This sensor, which is also referred to as a matrix sensor, may be incorporated in a camera 19 and it may be of the charge-coupled device (CCD) or of the complementary metal oxide semiconductor (CMOS) type. By way of example, the sensor 18 is constituted by a two-dimensional matrix of photoelectric elements. The sensor is generally associated with an electronic circuit for processing signals supplied by the photoelectric elements in order to deliver an analog, digital, or computer signal representative of the image received by the sensor. This signal representative of the image received by the sensor can then be delivered to an image processor device and/or to a display device and/or to an image storage device (not shown). The sensor 18 is generally associated with an optical objective system 20, which may include one or more optical elements, in particular one or more thin lenses, and possibly a diaphragm, associated to enable an image to be formed on the sensor.

In the example of FIGS. 1A to 1C, the optical objective system 20 associated with the sensor 18 is a telecentric objective system. Such a telecentric objective system is well known to the person skilled in the art of industrial display devices since it is used for forming on the sensor an image that has no or practically no parallax effect. In optical theory, a telecentric objective system is an objective system for which the inlet pupil is located at infinity. It follows that such an objective system observes in its field of view using observation rays that are parallel or almost parallel, whence the absence of any parallax effect. The optical axis of the objective system 20 preferably coincides with the installation axis A'1. Nevertheless, it is possible to imagine that the optical axis is not rectilinear, but rather segmented, e.g. by incorporating a deflector mirror in the objective system. Provision can thus be made for a deflector mirror at 45° relative to the installation axis, so as to have a first optical axis segment beside the sensor that is arranged at 90° relative to the installation axis, and a second segment on the other side of the deflector mirror that is arranged to match the installation axis A'1.

In FIGS. 1A to 1C, the optical system is arranged vertically along an axis A'1, and it faces downwards in order to observe the installation zone under the device, and thus observe any container 14 arranged in the installation zone. The photoelectric sensor 18 is thus at the top of the display device and it faces downwards towards the installation zone. With this configuration, it can be understood that the theoretical ring surface of a container 14 placed in the installation zone is thus contained in a plane that is parallel to the plane of the sensor. Thus, with a single telecentric objective system, and without any other optical system, the image of the ring surface that is formed on the sensor cannot "see" a defect of planeness. On the contrary, no variation in the height of the ring surface can be seen.

Thus, in the invention, the optical system 24 is interposed between the installation zone for the container and the sensor in order to form on the sensor an image of the ring surface of such a container placed in the installation zone. In addition to the optical objective system 20, the optical system includes at least one optical element 22 that, in this example, is arranged between the objective system 20 and the installation zone. The entire optical system 24 between the sensor 18 and the installation zone thus comprises the objective system 20 and the optical element(s) 22.

For practical purposes, the installation axis A'1 is defined as extending the optical axis of the optical system 24 within the installation zone.

In the example shown, the sensor 18, its objective system 20, the optical element 22, and the installation zone are in alignment in that order along the same installation axis A'1.

In an aspect of the invention, the method includes the steps consisting in forming a plane image of the ring surface on the sensor by means of an optical geometrical transformation (through the optical system 24 in this example) serving to convert the real ring surface into a ring surface image. The same transformation theoretically converts the theoretical ring surface into a theoretical ring surface image, in the sense that the theoretical ring surface image is the image that would be formed by applying the transformation to a real ring surface that coincides with the theoretical ring surface. This optical geometrical transformation, an example of which is shown in FIG. 3, converts a real height difference dZ along the direction of the theoretical central axis between a point under consideration T of the real ring surface and a corresponding point T of the theoretical ring surface into an image radial offset dR in the image of the image point IT' of the image of the ring surface of the container relative to the corresponding image point IT of the theoretical ring surface image. The corresponding point T of the theoretical ring surface is the point of the theoretical surface that has the same angular coordinate as the point under consideration T' in a cylindrical coordinate system centered on the theoretical central axis. The image point IT' of the image of the ring surface of the container is the image of the point under consideration T' of the real ring surface as seen through the optical system and as results from the optical geometrical transformation. The corresponding image point IT of the theoretical ring surface image is the image of the corresponding point T of the theoretical ring surface as seen through the optical system and as a result of the optical geometrical transformation.

Preferably, the optical geometrical transformation does not affect the relative angular positioning of two points of the surface of the ring around the axis, in the sense that two points of the real ring surface that are separated by an angular difference around the theoretical central axis have their respective images in the image that is obtained by the optical geometrical transformation likewise spaced apart by the same angular difference about the image of the theoretical central axis.

In the example shown in FIGS. 1A to 1C, the optical element 22, which performs the major part of this optical transformation, comprises a primary reflection surface 26, the primary surface 26 being a surface of revolution about the installation axis A'1 and being arranged to reflect light rays coming from the real ring surface towards the sensor. The primary reflection surface 26 thus possesses specular properties. It may advantageously be formed by a mirror, however it could also be made in the form of a prism, i.e. an optical interface surface.

The installation axis A'1 may be defined as being the axis of symmetry of revolution of the primary reflection surface 26.

In this first example, light rays coming from the surface of the real ring are reflected towards the sensor by reflection that is direct, i.e. without any other reflection surface.

In the example shown in FIGS. 1A to 1C, the primary reflection surface 26 is a surface of revolution facing away from the installation axis A'1 and flared towards the installation zone. More precisely, the primary reflection surface 26 comprises a convex frustoconical surface having a small diameter and a large diameter that are both smaller than the diameter of the theoretical ring surface. The small diameter is arranged closer to the sensor along the installation axis, while the large diameter is arranged closer to the installation zone.

In an aspect of the invention, because of this optical geometrical transformation, the image radial offset in the image plane picked up by the sensor and resulting from a unit real height difference is greater than the image radial offset resulting from a real radial offset of the same size between a point under consideration of the real ring surface and a corresponding point of the theoretical ring surface. In other words, the influence of a real height difference is greater than the influence of a real radial difference in the image radial offset that is obtained after the optical geometrical transformation. Thus, a height offset of 1 millimeter (mm) for the real ring surface relative to the theoretical ring surface gives rise to a first image radial offset, while a radial offset of 1 mm of the real ring surface relative to the theoretical ring surface gives rise to a second image radial offset, and in the invention the first image radial offset is greater than the second image radial offset.

In the device of the invention, this preponderance is provided by the fact that the optical system defines a peripheral observation field that observes the ring surface from above using radial observation rays contained in a radial plane containing the installation axis and forming an observation elevation angle relative to a plane PRef perpendicular to the installation axis A'1 that is in any event less than 45° and that is preferably less than 25°.

The peripheral observation field is preferably without any azimuth interruption around the installation axis A'1. In particular, there is no azimuth angular discontinuity between two observation radial rays that are infinitely close together angularly around the installation axis. As a result, there is no viewpoint interruption in the image, which would make the image difficult to interpret.

The peripheral observation field is also preferably continuous in azimuth in the sense that no azimuth observation angle around the installation axis is masked. Nevertheless, in certain circumstances, in particular because of hardware installation constraints, it may happen that one or more angular sectors around the installation axis are masked, while avoiding any azimuth interruption. Preferably, such a masked azimuth angular sector is of small or very small extent, preferably less than 10 degrees, more preferably less than 5 degrees around the installation axis.

An embodiment of this peripheral observation field is shown in FIG. 1A. This observation field extends over 360° C. around the installation axis A'1. This field observes "from above" in the sense that the ring surface is observed from above a plane Pref that is perpendicular to the theoretical central axis A1 of the ring surface, and tangential at at least one point to the ring surface, preferably its highest point along the direction of the theoretical central axis A1. The observation elevation angle corresponds to the angle ɣ relative to a plane perpendicular to the installation axis A'1 of an observation ray coming from the ring surface and suitable for being seen by the sensor through the optical system 24. In the context of the device having a telecentric optical system, the observation rays seen by the sensor all enter the objective system in parallel. Furthermore, if the primary reflection surface 26 is a frustoconical surface generated by a straight line, as in the system shown in FIG. 1, then the observation elevation angle ɣ is the same angle for all observation rays, and can be deduced directly from the angle of inclination of the primary reflection surface 26 relative to the installation axis A'1.

Nevertheless, as explained below for a device that does not have a telecentric objective system, or in which the optical element 22 is not strictly a cone generated by a straight line, the observation rays seen by the sensor may have different observation elevation angles from one another. Under all circumstances, it is possible to use the convention that the observation elevation angle is the largest angle relative to a plane perpendicular to the installation axis A'1 of an observation ray coming from the ring surface 16 and suitable for being seen by the sensor 18 through the optical system 24.

In the embodiment of the device of the invention shown in FIG. 1A that has a frustoconical primary reflection surface 26 that is convex in a plane perpendicular to the installation axis, this property whereby the influence of a difference in real height is greater than the influence of a real radial difference in the image radial offset obtained by the optical geometrical transformation is ensured in particular by the angle of the primary reflection surface 26 relative to the installation axis A1. More precisely, the half-angle at the apex • characteristic of the convex primary reflection surface 26 determines the ratio of the influence on the image radial offset between a height difference and a radial difference of the real surface relative to the theoretical ring surface. The closer this half-angle at the apex • comes to 45°, the greater the influence of the height difference on the image radial offset. Naturally, care should nevertheless be taken to ensure that this half-angle at the apex remains less than 45° so that the optical element 22 that carries the primary reflection surface 26 can be arranged above the ring surface 16, so that the sensor 18 thus sees the ring surface 16 from above through the optical system 24. Under all circumstances, this half-angle at the apex • is greater than 22.5° in order to ensure that the influence of a real height difference is greater than the influence of a real radial offset in the image radial offset.

The primary reflection surface need not be frustoconical but could be a flared surface of revolution having double curvature generated by sweeping a segment with a non-straight curve around the installation axis A'1, e.g. a segment of a parabola, a hyperbola, or an ellipse. By way of example, in a radial plane, this surface may present a profile that is concave or convex while conserving its convex profile in a plane perpendicular to the installation axis A'1. Such a surface with double curvature may be used in particular to make the system 24 as a whole telecentric relative to the sensor, even if the objective system 20 itself is not telecentric.

Preferably, in the method of the invention, the image radial offset corresponding to a unit real height difference is at least 2.14 times greater and preferably at least three times greater than the image radial offset corresponding to a real radial offset of the same dimension between said point of the real ring surface and a corresponding point of the theoretical ring surface. As a result, it is ensured that in the resulting image the great majority of a radial offset is due to an offset in height of the real ring surface relative to the theoretical ring surface, rather than to a radial offset between those two surfaces.

In the device of FIG. 1A, this ratio of three in the optical geometrical transformation corresponds to a half-angle at the apex of the primary reflection surface that is greater than 35.785°. This value makes it possible to obtain an observation elevation angle of less than 18.43°. In the embodiment shown in FIG. 1A, the observation elevation angle is 15°, and the half-angle at the apex • of the primary reflection surface 26 is 37.5°. More generally, the convex primary reflection surface 26 may be a frustoconical surface of revolution that is continuous over 360° around the installation axis A'1 and that presents a half-angle at the apex • that is equal to 45° minus half of the observation elevation angle.

The reflection surface 26 is preferably without discontinuity of curvature around the installation axis A'1, where curvature is analyzed in a plane perpendicular to the installation axis A'1, in order to ensure an observation field without azimuth interruption.

The reflection surface 26 is also preferably continuous in azimuth in the sense that it is continuously reflective about the installation axis A'1 without any masked sector, in order to ensure azimuth continuity for the observation field.

In another aspect of the invention, the viewing method provides for the real ring surface 16 of the container to be lighted using an incident light beam that is peripheral, i.e. extending over 360° around the installation axis A'1. The ring surface is lighted from above, in the sense that the incident light rays reach the ring surface 16 coming from points that are situated above the plane PRef perpendicular to the theoretical central axis A1 and tangential to a point of the ring surface, preferably its highest point along the direction of the theoretical central axis A1. This peripheral incident light beam comprises incident radial light rays contained in a radial plane containing the installation axis, said incident radial rays being directed towards the axis, as shown in FIG. 1B. The incident radial rays could be parallel rays, but that is not essential, and in the method as shown in FIG. 1B, the peripheral incident light beam comprises non-parallel radial rays in a given radial half-plane Pr (shown in FIG. 1C) that contains the installation axis and that is defined by the installation axis. Some of the radial rays are directed towards the installation axis without necessarily being perpendicular thereto. In contrast, FIG. 1B shows that the peripheral incident light beam may contain radial rays that form an elevation angle relative to a plane perpendicular to the installation axis that preferably lies in the range 0 to 45 degrees. Preferably, the light beam contains radial rays over an angular spread that is continuous or substantially continuous. This spread may have an angular extent of at least 30 degrees, or even more. The rays contained in this spread may form an elevation angle relative to a plane perpendicular to the theoretical central axis that lies in the range 5 degrees to 40 degrees.

In a device of the invention, the device thus includes a lighting system suitable for supplying such a peripheral incident light beam comprising radial rays contained in a radial plane containing the installation axis A'1. Preferably, this lighting system comprises an annular light source 28 having the installation axis A'1 as its axis. It preferably presents a diameter that is greater than the diameter of the real ring surface of the containers that are to be inspected using the device. This annular light source 28 is arranged above the installation zone, and thus above the real ring surface. In a radial half-plane Pr containing the installation axis A'1 and defined by the installation axis, the annular light source 28 corresponds to a source that could be a point source, or on the contrary that may have a certain extent in this half-plane Pr, as shown in the figures. This light source lights towards the installation zone, and thus towards the installation axis, but it forms relative to thereto an angle so as to direct lighting downwards. If the source is not a source emitting parallel rays, it is preferable for it to emit a light cone in this radial half-plane that contains radial rays over a continuous or substantially continuous spread, as shown in FIG. 1B. By way of example, this spread may form an angular sector over the range 5 degrees to 40 degrees relative to a plane perpendicular to the theoretical central axis. The angular extent of the spread may be limited by one or more masks. Nevertheless, the light source could emit over a much wider spread.

Insofar as the light source 28 is peripheral, it can be thought of as a multitude of sources, possibly point sources or quasi-point sources, arranged around the installation axis A'1 and each emitting a spread of light as defined above. The light source is preferably continuous over the entire 360° of periphery around the installation axis, in the sense that in each radial half-plane, it emits the same light spread. Nevertheless, in reality, a light source is not perfectly continuous. It can thus happen that it is interrupted over a preferably limited angular sector around the axis A'1. It may also happen that the light source is not continuous in the sense that it is made up by a series of individual sources that are juxtaposed and discrete, e.g. formed by a series of light-emitting diodes.

Preferably, the incident beam lights the ring surface 16 from above at an angle of incidence that is such that, at the point of reflection T of an incident ray, for which the ray reflected by the real ring surface is seen by the sensor, the normal "n" to the ring surface forms an angle of less than 30°, and preferably less than 10° relative to the axis A'1. In a configuration of perfect shape, with a real ring surface corresponding to the theoretical ring surface, this would ensure that the light reflected by the ring surface and seen by the sensor 18 is the light reflected by the point that is locally the highest or close to the point that is locally the highest of the ring surface. Consideration is given here solely to what happens in the radial half-plane Pr of the device and the ring surface to be inspected. Thus, the locally highest point of the ring surface is the point that, in the profile of the ring surface in this radial half-plane Pr, is the highest along the direction of the installation axis. Furthermore, the locally highest point is defined as being the point for which the normal to the ring surface is parallel to the installation axis. FIG. 1B shows an incident ray emitted by the light source and reflected by a point T' of the ring surface as a reflected ray that is intercepted by the primary reflection surface 26 and is thus sent towards the sensor by the optical system. By way of illustration, the normal "n" to the ring surface 16 at the point T' is substantially parallel to the direction of the installation axis, and the point T' is the locally highest point of the profile of the ring surface in the corresponding radial half-plane.

In the context of the device, this condition is satisfied by selecting a suitable position for the light source 28. By way of example, this position may be defined by the diameter of the light source 28 and by its height position along the direction of the installation axis A'1, thereby defining the angle of incidence of the rays that can light the ring surface. Naturally, the diameter and the height position of the real ring surface 16, in combination with the orientation of the normal at the point of reflection on the ring surface determine which ray(s) emitted by the source 28 will be reflected towards the sensor. It can thus be understood that for each ring surface diameter, it is necessary to adapt either the diameter of the light source or its height position relative to the ring surface 16. Nevertheless, it is not necessarily critical to detect the locally highest point of the ring surface. Specifically, in the context of a ring surface that is plane and annular, the inner and outer radial edges of the ring surface are necessarily slightly rounded, which means that even if the point of reflection of the incident light is situated on such a rounded portion, the difference in height between the reflection point and the locally highest point is generally considered as being negligible. In the context of a ring surface of profile in the radial half-plane that is rounded, it is also considered that the fact that the reflection takes place on a point that is not the locally highest point is largely compensated by the fact that this situation is repeated over the entire 360° of the periphery such that from the point of view of analyzing planeness, the error as committed in this way can generally be considered as being negligible. Thus, although it is possible to make provision for a device in which the light source is adjustable by adjusting its radial position or its position along the direction of the installation axis, so as to adjust the angle of incidence of the light beam on the ring surface, such provision is not necessary. Provision can thus be made to have a device in which there exists a singular annular light source having a defined diameter and a position that is fixed along the direction of the installation axis. Under such circumstances, the diameter of the annular light source 28 and its position along the direction of the axis are advantageously selected so as to satisfy the above condition, either for a mean ring surface diameter of the containers for inspection, or to correspond to a preferred ring surface diameter corresponding to the containers that are inspected the most frequently by the device. In a variant, in order to cover as well as possible a large range of ring surface diameters, it is possible to provide for the device to have a plurality of annular light sources, e.g. offset along the direction of the installation axis and/or of different diameters, these different light sources being capable of being used simultaneously or alternatively as a function of the ring surface diameter of a container for inspection.

Figure 2B:
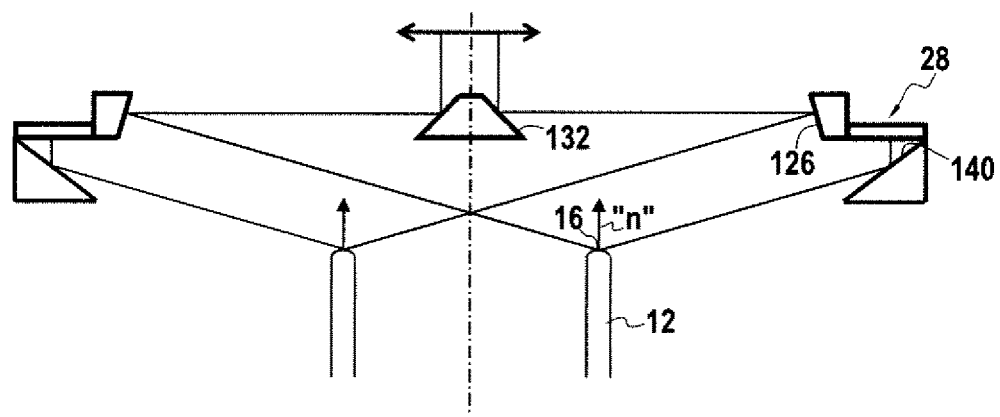
FIG. 2B is a view similar to FIG. 1B, showing a variant of the second device of the invention.

FIGS. 2A and 2B show a second embodiment of a device of the invention having a primary reflection surface 126 and a deflector reflection surface 132, suitable for performing a second method of the invention.

The image acquisition system, including the sensor 18, its objective system 20, and the optional image processor, display, and/or storage devices are identical to those described with reference to the embodiment of FIG. 1 and are therefore not described again in the context of this second embodiment. Likewise, the same lighting systems can be used in both embodiments, and the lighting system is not described in detail, except for the variant shown in FIG. 2B.

In this second embodiment, the optical system 124, which is arranged between the sensor 18 and the installation zone, presents a primary reflection surface 126 in the form of a surface of revolution facing towards the installation axis. This surface of revolution flares in the direction of the installation axis and it presents a small diameter and a large diameter, both of which are greater than the diameter of the theoretical ring surface. In this way, the primary reflection surface 126 can reflect light rays towards the installation axis A'1 that come from the real ring surface at the observation elevation angle •.

In this second embodiment, the device includes at least one second reflection surface between the primary reflection surface 126 and the sensor 18. As can be seen in FIG. 2A, the rays reflected by the primary reflection surface 126 are intercepted by a deflector reflection surface 132. The deflector reflection surface 132 is arranged in the field of view of the sensor, this field of view being defined by the optical objective system 20. In the example, this deflector reflection surface 132 comprises a surface of revolution facing away from the installation axis A'1, so as to deflect the rays towards the sensor.

In this embodiment, and unlike the first embodiment, even though the primary surface 126 is a surface of revolution having the installation axis A'1 as its axis, it is arranged to reflect light rays coming from the real ring surface at the observation elevation angle $\gamma$ towards the sensor 18 indirectly. Specifically, the reflection on the primary surface 126 is indirect since it is followed by at least one reflection prior to reaching the sensor 18, in this example a reflection on the deflector reflection surface 132.

In the embodiment shown, the primary reflection surface 126 is a portion of a frustoconical, surface that is concave in a plane perpendicular to the installation axis A'1. By way of example, it is formed on the inside surface of an annulus 122.

As for the first embodiment, the primary reflection surface 126 need not be frustoconical but could be a flared surface of revolution with double curvature, while still remaining concave in a plane perpendicular to the installation axis A'1.

In the embodiment shown, the deflector reflection surface 132 is a convex frustoconical surface having the installation axis A'1 as its axis. The deflector reflection surface 132 is formed on the outside surface of a truncated cone 134. In the example shown, it has a small diameter and a large diameter, both of which are smaller than the diameter of the ring surface of a container for inspection, but this characteristic is not essential. The large diameter lies below the small diameter. The deflector reflection surface 132 lies within the field of view of the sensor 18 as defined by the objective system 20.

In an advantageous embodiment, the path followed by rays between the primary reflection surface 126 and the deflector reflection surface 132 is perpendicular or substantially perpendicular to the installation axis. Such a provision serves to reduce considerably the sensitivity of the device to any centering defect of the primary reflection surface 126 or of the deflector reflection surface 132. For this purpose, the frustoconical deflector reflection surface 132 presents a half-angle at the apex of 45° and it is arranged at the same height along the direction of the installation axis A'1 as the primary reflection surface 126. The primary reflection surface 126 then presents a half-angle at the apex •' that is equal to half the desired observation elevation angle •. Thus, for a desired observation elevation angle ɣ of 15°, the primary reflection surface 126 presents a conical shape having its half-angle at the apex •' equal to 7.5°, the frustoconical primary reflection surface 126 flaring downwards, so that its large diameter lies below its small diameter along the direction of the installation axis.

Nevertheless, it is also possible to provide a variant of this second embodiment in which the deflector reflection surface 132 is a frustoconical surface that presents a half-angle at the apex β that is less than 45°, e.g. equal to 45° minus an angle •δ(Δ). Under such circumstances, the deflector reflection surface 132 is arranged above the level of the primary reflection surface 126, and the primary reflection surface 126 presents a half-angle at the apex •' that is equal to half the desired observation elevation angle • minus the value of the angle δ(Δ). If the value obtained in this way is negative, that means that unlike the preferred embodiment, the primary reflection surface 126 flares upwards, with its large diameter being arranged above its small diameter.

In the two above-described example devices, it is ensured that the ring surface is observed by the sensor 18 through the optical system 24 or 124 with a grazing observation elevation angle •ɣ, i.e. forming an angle that is small relative to a plane perpendicular to the installation axis, and preferably less than 25°, or smaller. Furthermore, in both embodiments, it can be seen that the ring surface 16 is observed "from the inside", i.e. that the observation rays on their path between the ring surface and the sensor, are directed towards the installation axis on leaving the ring surface 16 and going towards the primary reflection surface 26, 126. In contrast, the two embodiments differ in the sense that in the first embodiment the primary reflection surface 26 is arranged radially inside relative to the diameter of the ring surface, whereas in the second embodiment, the primary reflection surface 126 is arranged radially outside relative to the diameter of the ring surface 16. In the first embodiment, an observation ray coming from the ring surface 16 is intercepted by the primary reflection surface 26 in the same radial half-plane PRef following a short path. In the second embodiment, an observation ray coming from the ring surface 16 is intercepted by the primary reflection surface 126 at a point diametrically opposite from its origin point on the ring surface, following a long path that intersects the installation axis A'1. For a given observation elevation angle ɣ, it can be understood that the distance needed along the direction of the installation axis between the primary reflection surface 26 or 126 and the ring surface 16 is greater for the second embodiment than for the first embodiment.

In the second embodiment, the light source 28 is also an annular light source 28 presenting a diameter greater than the diameter of the ring surface. In the example shown, the diameter of the annular light source 28 is greater than the diameter of the annulus 122 carrying the primary reflection surface 126. In this embodiment, the light source 28 is arranged substantially at the same height along the direction of the installation axis as the primary reflection surface 126. Nevertheless, this position is purely illustrative, and it could be adapted as a function of the diameter and of the axial position of the ring surface of the container for inspection.

This second embodiment presents the advantage of making it possible to have an optical system 124 at a greater distance from the ring surface along the direction of the installation axis.

It may be observed that FIG. 2B shows a variant of the embodiment of FIG. 2A that differs solely by the fact that the lighting system includes, in addition to the annular light source 28, a reflector 140 that is arranged immediately below the annular light source 28. In this example, the reflector 140 comprises a frustoconical surface facing towards the installation axis. The surface of the reflector 140 flares upwards and thus presents a diameter that is substantially identical to the diameter of the light source 28. It reflects substantially vertical rays as emitted by the light source 28 towards the installation zone at a grazing angle of incidence, towards the ring surface. Such a reflector serves to concentrate the light emitted by the light source 28 onto the ring surface, at a grazing angle of incidence that is favorable for the invention.

FIG. 3 is a diagram showing the optical geometrical transformation performed by the optical system, which is shown in this example in the context of the second embodiment. There can thus be seen a difference between a point T' of the real ring surface 16 and a corresponding point T of the theoretical ring surface. In this example, this difference is a purely vertical distance dZ, and thus a difference that extends solely along the direction of the installation axis. The "theoretical" path of an observation ray coming from the point T of the theoretical ring surface and going towards the photoelectric sensor is represented by a continuous line, whereas the path of an observation ray coming from the point T' of the real ring surface is represented by a dashed line. In the bottom of FIG. 3, there can be seen the projection of the image I as seen by the sensor through the optical system, this image having a line I16 representing the theoretical ring surface image. The real ring surface image is shown in this example in the form of a line I16', which is the image formed by the optical system 24 or 124 on the sensor 18 of the reflection of the incident beam on the ring surface 16. The thickness of this line in the radial direction in the image is determined in particular by the shape (e.g. plane, rounded, upside-down V-shape, or polygonal), of the profile of the ring surface in section in a radial plane, by the extent of the light source in the same radial plane, and by the angle of the spread of light delivered by the source. The lines L1 and L2 show the limit of the observation field imposed by the optical system, in particular by the size of the primary reflection surface 126 along the direction of the installation axis. The real ring surface image I16', drawn in discontinuous lines, coincides substantially over the entire periphery with the theoretical ring image I16 drawn using a continuous line. However, it can be seen in the angular sector corresponding to the point T of the ring surface presenting a localized defect, that the real ring surface image I16' departs from the theoretical ring image I16 and, in the image, presents an image radial offset dR. It can be seen that the height difference dZ in the direction of the installation axis is converted by an optical geometrical transformation due to the optical system 124 into an image radial offset dR in the image seen by the sensor.

In the embodiment shown, this conversion may be written by the following relationship:

$$dR = dZ*G*\cos(•)$$

where G is the magnification of the objective system 20.

If an equivalent diagram is drawn to illustrate the influence of a radial difference between the real ring surface and the theoretical ring surface, it can be seen that the influence of this difference on the image offset dR is very small, being proportional to the sine of the observation elevation angle ɣ. Thus, by using an observation elevation angle of less than 25°, or indeed less than 18.43°, the influence of any such radial difference is considerably minimized.

It can be seen that the optical geometrical transformation proposed in the method of the invention and implemented by the optical system of the invention forms a complete and continuous optical image of the real ring surface on the sensor. This complete and continuous optical image is formed on the sensor without any digital transformation, solely by an optical method acting on light. In the example shown, this complete and continuous optical image is formed on the sensor by the optical system 24 without any digital transformation.

It should be observed that the optical system 24, and in particular the objective system 20, is focused on the ring surface 16 (ignoring strong astigmatism aberrations) so as to make the ring surface 16 conjugate with the sensor surface. The light rays coming from the source 18 and reflected on the ring surface 16 serve to form the image of the ring surface. They supply the necessary light.

In other words, the image of the ring surface I16' is preferably constituted by radial rays of the incident light rays that have been reflected by specular reflection on the ring surface 16 and directed onto the sensor 18 by the optical system 24 including in particular the primary reflection surface 26, 126. In certain embodiments, it is considered that the image I16' of the real ring surface is constituted solely by radial rays of the incident light beam that are reflected by specular reflection on the ring surface 16 and that are directed onto the sensor 18 by the optical system 24, including in particular the primary reflection surface 26, 126.

The image obtained by a device or a method of the invention can be used in the form of an image that is viewed. Thus, an operator can visually inspect such images in order to detect any ring surface defect and to determine the type of defect. Specifically, depending on the shape of the image of the real ring surface I16', it is possible for an operator to distinguish defects that are highly localized as compared with defects that are more widely spread.

In most situations, the image of the ring surface I16' can be thought of as a line, where it is possible to define a line I16' representative of the image of the ring surface, e.g. by selecting an inside or outside edge line or a middle line of the image of the ring surface as the representative line.

A theoretical line I16 representative of the theoretical ring surface image may be a predefined line, e.g. a circle centered on the image of the installation axis IA'1. The theoretical line I16 representative of the theoretical ring surface image may be deduced from the ring surface image I16', e.g. by calculation within an image processor device, by applying a digital transformation to this image seeking to estimate the corresponding theoretical line as a function of the ring surface image I16'.

From the image as obtained in this way, the method of the invention may include a determination step comprising determining an image radial difference between the line I16' representative of the image of the ring surface and the theoretical line I16 representative of the theoretical ring surface image. To do this, as the line representative of the image of the ring surface, it is possible to use the image of the reflection of the incident beam on the ring surface as formed by the optical system 24 or 124 on the sensor. In a device of the invention, this determination may be performed by an image processor device associated with the sensor 18, and including in particular a computer, for example.

FIG. 4 shows a third embodiment of the invention that differs from the first embodiment only in that the optical objective system 20 associated with the sensor 18 is not a telecentric objective system but a conventional objective system, for example, a system equivalent to the system to be found in a conventional camera and in which the entry pupil of the objective system is positioned within the objective system. Under such circumstances, it can be seen that the observation rays in the installation zone are no longer parallel to one another in a radial half-plane Pr, but on the contrary present a certain amount of divergence. Thus, for a given real height shift dZ, the observed offset dR varies with the distance of the ring from the axis A'1. As a result, a radial offset of the axis A1 of the ring relative to the axis A'1 of the installation leads to a complex modification in the shape of the real ring image (non-circular curve).

Whether or not the optical system 24, 124 is telecentric, the radial offset of the real ring surface relative to the axis of the installation gives rise to geometrical deformations of the image of the real ring. A telecentric system reduces and simplifies these deformations.

Compared with the theoretical ring surface image, the image of the real ring surface may thus combine a plurality of deformations, and in particular:

a) deformations associated with the real ring surface being off-center relative to the theoretical ring surface;

b) deformations associated with the real ring surface being ovalized;

c) defects associated with an angle of incidence of the real ring surface; and d) deformations associated with defects of planeness. It should be understood that because of the grazing angle of observation (small y), the deformations associated with planeness defects are maximized while the others can be ignored. Nevertheless, in order to improve accuracy, the processor system may identify and/or qualify and/or quantify the various deformations.

FIGS. 5A and 5B show images that can be obtained using a device or a method of the invention. Such images may be obtained directly on the sensor 18, directly merely by optical geometrical transformation through the optical system 24, and they comprise a real ring surface image I16 that is continuous over its entire periphery around the image of the theoretical central axis IA1.

In FIG. 5A, dashed lines show the image I16' of a real ring surface having its theoretical central axis A1 coinciding with the installation axis A'1. Under such circumstances, the theoretical ring image I16, drawn in continuous lines, is a perfectly circular image, and it is then easy to identify a defect of planeness by observing the image radial offset between the curves I16' and I16.

FIG. 5B shows the image I16' of a real ring surface having its theoretical central axis A1 offset radially and/or inclined relative to the installation axis A'1, for example. Under such circumstances, the theoretical ring image I16 is not a perfectly circular image, but is a closed curve that is off-center relative to the image of the installation axis IA'1. By way of example, the closed curve I16 is substantially oblong in shape. For this closed curve I16, it is possible to determine a center of gravity IA1 and from that center of gravity IA1 to determine a distance difference between an image point I16' of a real ring surface and a corresponding point having the same angular coordinate in the theoretical ring image I16. This distance can be used to determine a defect of planeness. Alternatively, it is possible to determine the geometrical transformation that serves to return the theoretical ring image I16 to a centered circle, and to apply that transformation to the real ring image I16', thereby returning to the situation of FIG. 5A by eliminating errors due to being off-center and/or to an angle of inclination.

FIG. 6 shows an inspection line 200 for inspecting containers 14 that makes use of a device 10 of the invention. In the example shown, the containers 14 are moved by a conveyor 210 that transports the containers 14 along a travel direction, e.g. in horizontal translation perpendicular to the theoretical central axes A1 of each of the containers 14. In the example shown, the conveyor 210 comprises a conveyor belt 212 on which the containers 14 are placed via their bottom surfaces, also referred to as a support plane, with their theoretical central axes A1 arranged vertically. The conveyor could alternatively comprise a conveyor wheel moving the containers 14 along a circular travel path, in particular in a horizontal plane. The conveyor 210 could also have guide means (not shown) co-operating with the side faces of the containers 14. The containers 14 thus present their ring surfaces 16 in an upwardly-facing horizontal plane. The conveyor 210 brings the containers along the horizontal path under the device 10 of the invention without any risk of interfering with the device 10. The device 10 may comprise a housing 230 containing in particular the sensor 18, the objective system 20, a primary reflection surface 126, and possibly a deflector reflection surface 132, as shown in FIG. 6. The housing 230 is arranged above the conveyor. Inside the housing 230, a device 10 of the invention is arranged with its installation axis A'1 in a vertical position, such that the field of observation and the incident light beam are oriented downwards towards the installation zone Z that is situated between the bottom face of the housing 130 and the conveyor belt 212. It can thus be understood that in this station, the conveyor 210 brings the containers so that their theoretical central axes A1 coincide as well as possible with the installation axis A'1. When they coincide, an image is acquired using the device 10 without that requiring any handling of the container or any stopping of the conveyor. The image acquired by the device 10 may then be sent to a processor system 240, e.g. an image processor device and/or a display device and/or an image storage device, e.g. a computer system including a computer. It is then possible to analyze the image as acquired in this way and to be able to identify, and even to quantify, a defect of planeness of the ring surface 16 of the container 14 in that image.

The device and the method thus do not involve physical contact with the container for inspection. A device of the invention is found to be less expensive and more compact than prior art devices, thus making it possible in particular for it to be installed easily in a station or a line for inspecting articles, which inspection station or line may include other devices for performing other inspections, and the inspection station or line can thus be installed in particular on a production line where the containers travel one after another. Such a device then makes it possible to inspect containers on a line, whether it be a container production line or a container processing line or a container filling line.

The device and the method of the invention may be performed using a single two-dimensional photoelectric sensor, e.g. a single camera, and still give information about the planeness of the entire ring surface, and this can be done from a single optical two-dimensional image acquired directly by the sensor, without requiring a plurality of optical images that are acquired distinctly.

The observation system of the invention is described herein in preferred embodiments in which the reflecting surfaces are mirrors. It is possible to envisage obtaining the same results by using prism-type optical elements, presenting surfaces that are likewise conical, for example, leading to total internal reflections. An optical element in the meaning of the invention may include a Fresnel lens. Such means also make it possible to observe with the same values for the angle $\gamma$, and it is possible with such means to arrange for observations to be telecentric or otherwise.

The invention is not limited to the examples described and shown, since various modifications can be made thereto without going beyond its ambit.

The invention claimed is:

1. A visualization method for visualizing the planeness of a real ring surface (16) of a container (14), the ring surface having a theoretical shape that is plane and annular or circular around a theoretical central axis (A1), and the method being of the type comprising the steps consisting in:
   lighting the real ring surface (16) of the container with a peripheral incident light beam; and
   using an optical system (24, 124) to form a plane image of the ring surface of the container on a two-dimensional photoelectric sensor (18);
   the method being characterized in that:
   the peripheral incident light beam comprises radial light rays contained in a radial plane containing the theoretical central axis (A1), said radial rays being directed towards the theoretical central axis (A1);
   the peripheral incident light beam lights the ring surface (16) from above, and radial rays of the incident light beam are reflected by specular reflection the ring surface (16);
   in that the step consisting in forming a plane image includes an optical geometrical transformation that converts the real ring surface (16) into a ring surface image (I16'), this transformation theoretically converting the theoretical ring surface into a theoretical ring surface image (I16);
   in that the optical geometrical transformation converts a real height difference (dZ) along the direction of the theoretical central axis (A1) between a point under consideration (T') of the real ring surface (16) and a corresponding point (T) of the theoretical ring surface into an image radial offset (dR) in the image of the image point (IT') of the ring surface image of the container relative to the corresponding image point (IT) of the theoretical ring surface image; and
   in that, in the plane image, the image radial offset (dR) corresponding to a unit real height difference (dZ) is greater than the image radial offset corresponding to a real radial offset of the same dimension between said point under consideration (T') of the real ring surface and a corresponding point (T) of the theoretical ring surface.

2. A visualization method according to claim 1, characterized in that the image radial offset (dR) corresponding to a unit real height difference (dZ) is at least three times greater than the image radial offset corresponding to a real radial offset of the same dimension between a point under consideration of the real ring surface and a corresponding point of the theoretical ring surface.

3. A visualization method according to claim 1, characterized in that the method includes the step of observing the real ring surface (16) by means of the optical system (24, 124) at an observation elevation angle ($\gamma$) of less than 25° relative to a plane perpendicular to the theoretical central axis (A1).

4. A visualization method according to claim 1, characterized in that the method includes the step of observing the real ring surface (16) by means of the optical system (24, 124) at an observation elevation angle (ϒ) of less than 18.43° relative to a plane perpendicular to the theoretical central axis (A1).

5. A visualization method according to claim 1, characterized in that the optical system (24, 124) defines a peripheral observation field that observes the ring surface (16) by radial observation rays that are contained in a radial plane containing the theoretical central axis (A1) and forming, relative to a plane perpendicular to the theoretical central axis (A1), a theoretical central angle of less than 25°.

6. A visualization method according to claim 5, characterized in that the observation elevation angle is less than 18.43° relative to a plane perpendicular to the theoretical central axis.

7. A visualization method according to claim 3, characterized in that the optical system (24, 124) includes a primary reflection surface (26, 126), the primary reflection surface (26, 126) being a surface of revolution having the theoretical central axis (A1) as its axis and arranged to reflect light rays coming from the real ring surface at the observation elevation angle directly or indirectly towards the sensor.

8. A visualization method according to claim 1, characterized in that the step consisting in forming a plane image (I) includes optically forming a complete and continuous two-dimensional image (I16') of the real ring surface (16).

9. A visualization method according to claim 1, characterized in that the peripheral incident light beam includes non-parallel radial rays in a common radial plane.

10. A visualization method according to claim 1, characterized in that the incident beam lights the ring surface at an angle of incidence such that, at the point of reflection of an incident ray giving rise to a ray reflected by the real ring surface (16) that is seen by the sensor, the normal ("n") to the ring surface (16) forms an angle of less than 30° relative to the direction of the theoretical central axis (A1).

11. A method of determining the planeness of a real ring surface (16) of a container (14), the ring surface (16) having a theoretical shape that is plane and annular about a theoretical central axis (A1), the method being characterized in that it includes the visualization method according to claim 1, and in that the method includes a determination step comprising determining an image radial offset (dR) between a line (I16') representative of the image of the ring surface (16) and a theoretical line (I16) representative of the theoretical image of the ring surface.

12. A determination method according to claim 11, characterized in that the line (I16) representative of the ring surface image is the image formed by the optical system (24, 124) on the sensor (18) of the reflection of the incident beam on the ring surface (16).

13. A display device for viewing the planeness of a real ring surface (16) of a container (14), the ring surface having a theoretical shape that is plane and annular or circular around a theoretical central axis (A1), the device (10) being of the type in which it presents an installation zone for installing a container, said installation zone having an installation axis (A'1), of the type comprising:
  a lighting system (28, 140) suitable for supplying a peripheral incident light beam having radial rays contained in a radial plane containing the installation axis (A'1), said radial rays being directed towards the installation axis (A'1);
  a two-dimensional photoelectric sensor (18); and
  an optical system (24, 124) interposed between the container installation zone and the sensor (18) and suitable for forming on the sensor (18) an image (I16') of the ring surface (16) of a container (14) placed in the installation zone;
  and of the type in which the lighting system (28, 140), the sensor (18), and the optical system (24, 124) are arranged above the installation zone;
  the device being characterized in that the optical system (24, 124) defines a peripheral observation field that observes the ring surface (16) with radial observation rays that are contained in a radial plane containing the installation axis (A'1) and that form an observation elevation angle of less than 25 degrees relative to a plane perpendicular to the installation axis (A'1); and
  in that the lighting system comprises a light source (28) having the installation axis (A'1) as its axis and presenting a diameter greater than the diameter of the ring surface (16).

14. A device according to claim 13, characterized in that the device includes a single two-dimensional photoelectric sensor (18) on which a complete and continuous image (I16') of the real ring surface (16) is formed.

15. A device according to claim 13, characterized in that the device (10) includes a primary reflection surface (26, 126), the primary reflection surface (26, 126) being a surface of revolution having the installation axis (A'1) as its axis and arranged to reflect light rays coming from the real ring surface (16) at an observation elevation angle directly or indirectly towards the sensor (18).

16. A device according to claim 15, characterized in that the primary reflection surface (126) reflects light rays indirectly towards the sensor (18), and in that the device includes at least one second reflection surface (132) between the primary reflection surface (126) and the sensor (18).

17. A device according to claim 15, characterized in that the primary reflection surface (26) comprises a surface of revolution facing away from the installation axis and presenting a small diameter and a large diameter, both of which are smaller than the smallest diameter of the theoretical ring surface.

18. A device according to claim 17, characterized in that the primary reflection surface (26) is a convex frustoconical surface presenting a half-angle at the apex (α) equal to 45° minus half the observation elevation angle (ϒ).

19. A device according to claim 15, characterized in that the primary reflection surface (126) comprises a surface of revolution facing towards the installation axis (A'1) and presenting a small diameter and a large diameter, both of which are greater than the greatest diameter of the theoretical ring surface so as to deflect light rays coming from the real ring surface (16) at an observation elevation angle (ϒ) towards the installation axis (A'1), said rays being intercepted by a deflector reflection surface (132) that comprises a surface of revolution (132) facing away from the installation axis (A'1) so as to deflect the rays towards the sensor (18).

20. A device according to claim 16, characterized in that the path followed by the rays between the primary reflection surface (126) and the deflector reflection surface (132) is perpendicular to the installation axis (A'1).

21. A device according to claim 20, characterized in that the deflector reflection surface (132) comprises a convex frustoconical surface of revolution having the installation axis (A'1) as its axis and presenting a half-angle at the apex (β) of 45°.

22. A device according to claim 19, characterized in that it includes a telecentric optical system (20) between the sensor (18) and the primary reflection surface (126).

23. A device according to claim 13, characterized in that the incident peripheral beam comprises non-parallel radial rays in a common radial plane (Pr).

24. A device according to claim 13, characterized in that the light source (28) is an annular source forming a body of revolution having the installation axis (A'1) as its axis.

25. A device according to claim 13, characterized in that the device (10) has a housing (230) containing the sensor (18), the objective system (20), a primary reflection surface (126), and optionally a deflector reflection surface (32).

26. An inspection line (200) for inspecting containers (14) each presenting a ring surface (16), the line being of the type in which the containers (14) are moved on a conveyor line by a conveyor (210) that transports the containers (14) in a horizontal travel direction perpendicular to a theoretical central axis (A1) of each container (14), such that the containers thus present their ring surfaces (16) in an upwardly-facing horizontal plane, the line being characterized in that the installation includes a device (10) according to claim 13, that is arranged on the installation with its installation axis (A'1) in a vertical position, in such a manner that the observation field and the incident light beam are downwardly oriented towards the installation zone (Z) which is situated between the device and a transport member of the conveyor (212).

27. An inspection line (200) according to claim 26, characterized in that the conveyor (210) brings the containers in such a manner that their theoretical central axes (A1) coincide with the installation axis (A'1), and when they coincide, an image is acquired using the device (10) without the device (10) contacting the container (14).

* * * * *